United States Patent [19]

Anichkov et al.

[11] 4,228,799

[45] Oct. 21, 1980

[54] METHOD OF GUIDING A STEREOTAXIC INSTRUMENT AT AN INTRACEREBRAL SPACE TARGET POINT

[76] Inventors: Andrei D. Anichkov, ulitsa Blokhina, 6/3, kv. 4; Jury Z. Polonsky, ulitsa Komsomola, 16, kv. 24; Vladimir V. Usov, Degtyarny pereulok, 26, kv. 3, all of Leningrad, U.S.S.R.

[21] Appl. No.: 945,209

[22] Filed: Sep. 22, 1978

[30] Foreign Application Priority Data

Sep. 28, 1977 [SU] U.S.S.R. ............... 2528446

[51] Int. Cl.$^3$ ............................................. A61B 6/02
[52] U.S. Cl. ................................................. 128/303 B
[58] Field of Search ................... 128/303 B, 654, 754, 128/92 R, 92 A, 92 EA; 250/312

[56] References Cited

U.S. PATENT DOCUMENTS

| | | | |
|---|---|---|---|
| 3,357,431 | 12/1967 | Newell | 128/303 B |
| 3,457,922 | 7/1969 | Ray | 128/303 B |
| 3,508,552 | 4/1970 | Hainault | 128/303 B |

FOREIGN PATENT DOCUMENTS

| | | | |
|---|---|---|---|
| 107206 | 8/1963 | Netherlands | 128/303 B |
| 527189 | 9/1976 | U.S.S.R. | 128/303 B |

OTHER PUBLICATIONS

"Introduction in Stereotaxic with Atlas of the Human Brain", *Stereotaxic Instruments*, Riechert et al., vol. I, Stuttgart, Germ., 1959.

*Primary Examiner*—Robert W. Michell
*Assistant Examiner*—J. Kruter
*Attorney, Agent, or Firm*—Haseltine, Lake & Waters

[57] ABSTRACT

A method for guiding a stereotaxic instrument at a target point in an intracerebral cavity comprising fixing detachable roentgenocontrast markers with respect to the patient's cranium, then effecting contrast roentgenography and determining the relative position of the markers and intracerebral reference points. Subsequently, the position of a target point with respect to the intracerebral reference points is determined and a physical model of the intracerebral cavity is constructed to include the points simulating the markers and a point simulating the target point. A stereotaxic apparatus is installed on the patient's head, the detachable roentgenocontrast markers are again fixed with respect to the patient's cranium, the position of the detachable markers with respect to the stereotaxic apparatus is identified and the positions of the detachable roentgenocontrast markers with respect to the stereotaxic apparatus are set-up in the model of the stereotaxic apparatus. The physical model of the intracerebral cavity is then oriented with respect to the model of the stereotaxic apparatus, a guiding device with a stereotaxic instruments is installed in the model of the stereotaxic apparatus, the active end of the stereotaxic instrument is brought into registry with the point of the physical model of the intracerebral cavity simulating the target point, and the position of the stereotaxic instrument in the guiding device is fixed. A trepanation opening is then formed and the guiding device with the stereotaxic instrument is mounted on the stereotaxic apparatus and the stereotaxic instrument is introduced into the trepanation opening.

6 Claims, 12 Drawing Figures

METHOD OF GUIDING A STEREOTAXIC INSTRUMENT AT AN INTRACEREBRAL SPACE TARGET POINT

FIELD OF THE INVENTION

The present invention relates generally to the field of medicine, and more specifically, to methods of guiding a stereotaxic instrument at an intracerebral space target point, and may find application in stereotaxic operations performed on the brain in humans.

The term "target point" is defined herein as an intracerebral space point located in the region of a cerebral structure to be subjected to stereotaxic effect.

The term "guiding a stereotaxic instrument at a target point" is defined herein as imparting to a stereotaxic instrument such a spatial position which, if the stereotaxic instrument has been set appropriately in a stereotaxic apparatus, will ensure the adjustment matching of the stereotaxic instrument to the intracerebric space target point, as well as the adjustment matching proper.

BACKGROUND OF THE INVENTION

In the prior state of the art there is known a method of guiding a stereotaxic instrument at a target point incorporating the employment of a stereotaxic apparatus disclosed in U.S.S.R. Inventor's Certificate No. 283,494, and a method similar to it incorporating the employment of a stereotaxic surgical apparatus disclosed in U.S. Pat. No. 3,457,922. The method in question comprises injecting a roentgenocontrast substance into the ventricles of the patient's brain, movably securing to the patient's head a stereotaxic instrument, X-raying the patient's head in two projections, identifying through the coordinate system definable by the intracerebral reference points a position of the target point in the coordinate system of the X-ray pictures, spatially locating a relative position of the target point and the stereotaxic instrument by the projections thereof on the X-ray pictures, moving the stereotaxic instrument for the purpose of assigning thereto such a spatial position as required for guiding at the target point, recurrently X-raying for the purpose of spatially locating a position of the target point and stereotaxic instrument after having it moved, and matching the stereotaxic instrument to the intracerebral space target point.

A disadvantage of the aforedescribed method consists in the low accuracy of spatially locating a position of the target point in the coordinate system involving the X-ray pictures owing to the absence of control over the orthogonality of the coordinate system involving the X-ray picture, the coordinate system defined by the intracerebral reference points and also the low accuracy of spatially locating the relative position of the target point and stereotaxic instrument by their projections on the X-ray pictures, inasmuch as it is next to impossible to guarantee the orthogonality of the coordinate system involving the stereotaxic apparatus, and by the coordinate system involving the X-ray picture. Hence, the accuracy of guiding the stereotaxic instrument at the target point will be insufficient in the above method. Another disadvantage of the method is the high degree of traumatization caused by the lengthy procedure of guiding and the necessity of exposing the patient to repeated irradiation in the course of the guiding procedure.

In the prior art there is known a method of guiding a stereotaxic instrument at a target point incorporating the employment of a stereotaxic neurosurgical apparatus disclosed in U.S. Pat. No. 3,357,431 comprising the steps of injecting an X-ray contrast substance into the ventricles of the patient's brain, movably fixing to the patient's cranium a stereotaxic instrument associated with two X-ray contrast point markers so that said markers and said stereotaxic instrument are established along the same straight line perpendicular to the mid-sagittal plane of the brain, X-raying the patient's cranium in two respectively perpendicular projections, locating by means of the coordinate system defined by the intracerebral reference points a spatial position of the target point in the coordinate system involving X-ray pictures, locating a spatial position of the target point relative to the X-ray contrast point markers, moving the stereotaxic instrument along the plane parallel to the mid-saggittal plane of the brain for the purpose of matching the projections of the X-ray contrast point markers to the projection of the target point on the profile X-ray picture and moving the stereotaxic instrument along the straight line perpendicular to the mid-saggital plane of the brain for the purpose of matching on the frontal X-ray picture the projection of the stereotaxic instrument to the projection of the plane parallel to the mid-sagittal plane of the brain and extending across the projection of the target point, and matching the stereotaxic instrument to the target point within the brain.

The guiding accuracy provided by this method is somewhat higher than that of the foregoing method, yet even this accuracy is not adequate by reason of the insufficiently high accuracy of locating, by means of the coordinate system defined by the intracerebral reference points, a spatial position of the target point in the coordinate system involving X-ray pictures since the orthogonality of the coordinate system involving the intracerebral reference points, the coordinate system involving X-ray pictures, fails to be controlled effectively. Another disadvantage of this method is the considerable traumatization resulting from the overly protracted guiding procedure. Furthermore, a disadvantage of the method described lies in the restrictions imposed on the availability of surgical access to the target point because upon matching the stereotaxic instrument to it, the instrument is capable of moving only along the plane parallel to the mid-sagittal plane of the brain.

Also known in the prior art is a method of guiding a stereotaxic instrument at a guiding point assuming the employment of a stereotaxic neurosurgery apparatus disclosed in U.S. Pat. No. 3,508,552 featuring the steps of injecting an X-ray contrast substance into the ventricles of the patient's brain, fastening to the patient's skull X-ray contrast markers made in the form of double grids with parallel rectangular passages forming a regular square pattern, X-raying the patient's skull in two respectively perpendicular projections, locating a spatial position of the target point in the coordinate system involving X-ray pictures by means of the coordinate system defined by the intracerebral reference points, determining in the grid arranged parallel to the mid-sagittal plane of the brain the specific rectangular passage having a projection thereof matched to a projection of the target point on the profile X-ray picture, determining in the grid arranged perpendicular to the mid-sagittal plane of the brain the specific rectangular passage having a projection thereof matched to a projection of the target point on the frontal X-ray picture, and adjusting the stereotaxic instrument to the target point within the brain by introducing the stereotaxic instrument through one of the specific rectangular passages of one of the grids to a depth corresponding to the distance from this grid to the other specific passage.

Disadvantages inherent in this method consist of the low accuracy of guiding a stereotaxic instrument, the objectionably high degree of traumatization and the limitations imposed on the availability of surgical access to the target point. The guiding accuracy provided by the present method is slightly lower than that of the preceding method owing to the fact that both of these methods are characterized by the insufficiently high accuracy of locating a spatial position of the target point in the coordinate system involving the X-ray pictures by means of the coordinate system defined by the intracerabral reference points, while the accuracy of matching the stereotaxic instrument to the target point is largely dependent on the dimensions of the rectangular passages and the distances between the adjacent passages. The traumatization level due to the time interval taken by the guiding procedure is somewhat lower in this method as compared to the foregoing one because the guiding procedure can be accomplished more quickly inasmuch as there is no need for repeated X-raying. The surgical access can be effected not only parallel to one plane, as in the preceding method, but parallel to two planes.

The abovementioned disadvantages are partially eliminated in a method of guiding a stereotaxic instrument at an intracerebral space target point described in a paper by T. Riechert "Die Stereotaktischen Hirnoperation", Deutsche Medischen Wissenschrift, 1959, vol. 84, pp. 1669–1683. This method contemplates injecting an X-ray contrast substance into the ventricles of the patient's brain, placing a stereotaxic apparatus on the patient's head, fastening detachable X-ray contrast markers to the patient's cranium, taking two X-ray pictures of the patient's head including an image of the intracerebral reference points under different projection conditions, locating a position of the intracerebral reference points relative to the X-ray contrast markers, locating a position of the intracerebral reference points relative to the target point, constructing an intracerebral space physical model including a point simulative of the target point and sequentially matching the stereotaxic instrument to the point of the physical model simulative of the target point and to the intracerebral space target point.

Subsequent to injecting an X-ray contrast substance the patient's head is placed movably in the stereotaxic apparatus made integral with an operation table and X-ray film holders. The base ring of the stereotaxic apparatus has four X-ray contrast point markers attached thereto and arranged along the two respectively perpendicular diameters of the ring. These markers define a coordinate system of the stereotaxic apparatus.

The injection of the X-ray contrast substance is effected through a specially drilled trepanation aperture.

The fastening of the X-ray point markers to the patient's cranium is effected by placing under X-ray control and rigidly fixing the patient's head in the stereotaxic apparatus. As this takes place, it is essential that the coordinate planes of the coordinate system defined by the intracerebral reference points be orthogonal to the planes of the X-ray films and the main rays of the X-ray tubes.

The X-ray pictures are taken simultaneously by two X-ray tubes when they are strictly centered with respect to the X-ray contrast point markers and the films.

The films obtained provide an image of the intracerebral reference points which is followed by constructing a coordinate system based on these points, determining the coordinates of the target point according to the stereotaxic atlas and plotting them on the films with allowance made for the enlargement coefficient of the films. A coordinate system of the stereotaxic apparatus is constructed by the projections of the four X-ray contrast point markers and the coordinates of the target point are determined in this system.

The intracerebral space physical model is constructed on the basis of a stereotaxic apparatus model representing an exact copy of the base ring of the stereotaxic apparatus. A point simulative of the target point is set forth in the intracerebral space physical model in the coordinate system of the stereotaxic apparatus.

The procedure of adjusting the stereotaxic instrument to the point of the intracerebral space physical model simulative of the target point is effected by transfering a guiding device with the stereotaxic instrument from the base ring of the stereotaxic apparatus onto the ring of the stereotaxic apparatus model. Making use of the available degrees of freedom of the guiding device therewith, the stereotaxic instrument is adjusted to the point simulative of the target point and this position of the stereotaxic instrument is fixed, whereafter the guiding device with the stereotaxic apparatus is again transferred onto the base ring of the stereotaxic apparatus and in the process of introducing the stereotaxic apparatus into the trepanation opening in the patient's skull the instrument is adjusted to the intracerebral space target point.

The aforedescribed method has significant disadvantages. Making X-ray films, determining the coordinates of the target point and adjusting the stereotaxic instrument thereto are to be accomplished as soon as the X-ray contrast substance is injected into the cavities of the patient's brain which causes the brain to swell and leads to a change of the spatial position of the cerebral structures relative to the intracerebral reference points as compared to their position specified in the stereotaxic atlas. Consequently, inaccuracy in the guiding procedure of the stereotaxic instrument may result. This disadvantage is also due to the necessity of very accurately placing the patient's head and centering the X-ray tubes, during which operations the coordinate planes of the coordinate system defined by the intracerebral reference points must be orthogonal to the planes of the films and the main rays of the X-ray tubes, which is impracticable in the actual conditions of neurosurgical intervention and brings about errors in the calculations.

Another disadvantage of the method described above is the high degree of traumatization. This is attributable to the necessity of rigidly fastening the patient's head, drilling a special trepanation opening for the injection of the X-ray contrast substance since with the patient's head being fastened it is impossible to inject a gasiform X-ray contrast substance through a lumbar puncture. The necessity of X-raying to check the fastening of the X-ray contrast markers to the patient's cranium and the adjustment of the stereotaxic instrument to the target point within the brain leads to a slow healing process of the operation injuries. The high degree of traumatization is produced due to the fact that the fastening of the patient's head, the injection of an X-ray contrast substance, the X-raying procedure, the handling of the films, the determination of the coordinates of the target point, the construction of the intracerebral space physical model and the adjustment of the stereotaxic instrument to the point of the physical model simulative of the target point are effected directly in the course of the neurosurgical operation, which, as a consequence, lasts not less than three hours. Throughout this time the patient is lying on the operation table with a trepanation opening.

The long duration of the operation does not permit guiding the stereotaxic instrument at more than three target points.

Further, when fastening the patient's head in the course of X-raying the contrasting qualities of the required cerebral cavities shown on the X-ray film are apt to deteriorate, which tends to complicate the identification of the intracerebral reference points to such an extent that occasionally it becomes indispensable either to utilize an X-ray contrast substance of improved contrasting qualities or to inject an X-ray contrast substance once again. Additionally, the rigid fastening of the head generally disagrees with certain patients, e.g. those suffering from epilepsy.

Other disadvantages of the aforesaid method consist in that in the X-raying process, the patient's head is placed in the stereotaxic apparatus comprising steel elements, which hamper the implementation of the X-raying process.

Further, in order to practice the method as described above it is necessary to have a specialized operating theater equipped with a special X-raying instrumentation, which can not be used for other purposes.

SUMMARY OF THE INVENTION

An object of the present invention is to increase the accuracy of guiding a stereotaxic instrument at an intracerebral space target point.

Another object of the invention is to reduce the degree of traumatization when guiding a stereotaxic instrument at a target point.

A further object of the invention is to cut down the duration of a stereotaxic operation.

Broadly stated, the invention resides in injecting a roentgenocontrast medium into the cavities of the patient's brain, securing to the patient's cranium at least four detachable roentgenocontrast markers having known distances therebetween; sequentially performing two roentgenographies under different projection conditions, removing the detachable roentgenocontrast markers from the patients head; identifying a position of the detachable roentgenocontrast markers relative to the intracerebral reference points by using the roentgenograms available from said roentgenographies, distances between the detachable roentgenocontrast markers and a position of the roentgen radiation source respective to the X-ray films in the course of said roentgenographies. Subsequently a position of the target point is identified with respect to the intracerebral reference points and an intracerebral space physical model is constructed, wherein included are three points adapted to simulate the three detachable roentgenocontrast markers, and a point adapted to simulate the target point. The method further comprises placing a stereotaxic apparatus on the patient's head, securing again to the patient's cranium the detachable roentgenocontrast markers in exactly the same position they had in the course of the roentgenographies, identifying a position of the detachable roentgenocontrast markers simulated in the intracerebral space physical model respective to the stereotaxic apparatus and fixing in a stereotaxic apparatus model the specified positions of the detachable roentgenocontrast markers respective to the stereotaxic apparatus. Subsequently the intracerebral space physical model is oriented relative to the stereotaxic apparatus model by placing the three points thereof adapted to simulate the three detachable roentgenocontrast markers in the specified positions of the detachable roentgenocontrast markers relative to the stereotaxic apparatus set forth in the stereotaxic apparatus model; mounting a guiding arrangement with a stereotaxic instrument upon the stereotaxic apparatus model, adjusting the operative end of the stereotaxic instrument to the point of the intracerebral space physical model adapted to simulate the target point, with the position of the stereotaxic apparatus being rigidly secured at the guiding arrangement; drilling a trepanation aperture, mounting the guiding arrangement with the stereotaxic instrument upon the stereotaxic apparatus and introducing the stereotaxic instrument into the trepanation aperture.

Advantages of the present invention are as follows. Owing to the possibility of reproducing a position of the detachable X-ray contrast markers relative to the patient's cranium the proposed method enables dividing in time the injection of a roentgenocontrast substance into the cavities of the patient's brain, performing the roentgenographies of the patient's head, identifying a position of the detachable roentgenocontrast markers relative to the intracerebral reference points and constructing an intracerabral space physical model, on one hand, and adjusting the stereotaxic instrument to the point of the physical model adapted to simulate the target point, and to the intracerebral space target point, on the other hand. While this takes place, a time interval between the stated groups of operations can be arbitrarily large and, as a consequence, sufficient for:

(a) the changes of the spatial position of the cerebral structures caused by the injection of the roentgenocontrast medium to vanish by the moment of adjusting the stereotaxic instrument to the intracerebral space target point which steps up the accuracy of guiding the stereotaxic instrument; and (b) the intracerebral space physical model can be constructed well before the adjusting procedure, which reduces the duration of the stereotaxic operation and, consequently, reduces the traumatization caused by the guiding method.

The accuracy of guiding the stereotaxic instrument is also improved due to the fact that in the proposed method the necessity of accurately placing the patient's head and strictly centering the X-ray tubes relative to the roentgenocontrast markers and the films, has been ruled out.

Since there is no need for rigidly fastening the patient's head to the operation table in the course of the roentgenographies, the risk of traumatizing the patient when he makes involuntary movements, as for instance, in an epileptic seizure, is avoided. In the proposed method there is no necesity for drilling a trepanation opening in the patient's skull because it affords a possibility of injecting a roentgenocontrast medium through a lumbar puncture.

In addition, the traumatization level in the proposed method is decreased since the procedure of adjusting the stereotaxic instrument to the target point is accomplished without exposing the patient to the X-ray radiation, which contributes to a speedy healing of his surgical wounds.

The steps of identifying the positions of the detachable roentgenocontrast markers, simulated in the intracerebal space physical model, relative to the stereotaxic apparatus, and fixing the specified positions of the detachable roentgenocontrast markers relative to the stereotaxic apparatus in the stereotaxic apparatus model can be effected by sequentially adjusting the stereotaxic instrument to the detachable roentgenocontrast markers while securing the positions of the stereotaxic instrument at the guiding arrangement at each such adjustment and transferring the guiding arrangement with the stereotaxic instrument after each such adjustment from the stereotaxic apparatus onto the stereotaxic apparatus model.

Such a procedure ensures simplicity and high accuracy in identifying the positions of the detachable roentgenocontrast markers relative to the stereotaxic apparatus and fixing these positions in the stereotaxic apparatus model. The stereotaxic apparatus and its model need not be equipped with additional appliances therewith.

According to an embodiment of the invention, it is contemplated that securing to the patient's cranium the detachable roentgenocontrast markers is preceded by fastening four complementary roentgenocontrast markers in the bones of his cranium, which is followed by performing said two roentgenographies; injecting a roentgenocontrast medium into the cavities of the patient's brain is effected subsequent to performing said roentgenographies and removing the detachable roentgenocontrast markers from the patient's head; injecting a roentgenocontrast medium into the cavities of the patient's brain is followed by sequentially performing two more roentgenographies differing in projection conditions; identifying a position of the detachable roentgenocontrast markers relative to the intracerebral reference points is effected on the basis of said four roentgenographies by means of identifying a position of the detachable roentgenocontrast markers relative to the complementary roentgenocontrast markers and identifying a position of the complementary roentgenocontrast markers relative to the intracerebric reference points, with distances between the complementary roentgenocontrast markers being calculated while identifying a position of the detachable roentgenocontrast markers relative to the complementary roentgenocontrast markers, a position of the detachable roentgenocontrast markers relative to the complementary roentgenocontrast markers being identified by using the roentgenograms available from the initial two roentgenographies, distances between the detachable roentgenocontrast markers and positions of the roentgen radiation source relative to the roentgen films in the course of the initial two roentgenographies, while a position of the complementary roentgenocontrast markers relative to the intracerebral reference points being identified by using the roentgenograms available from the second two roentgenographies, distances between the complementary roentgenocontrast markers and positions of the roentgen radiation source relative to the roentgen films in the course of the second two roentgenographies.

The fastening of the complementary roentgenocontrast markers as bones of the patient's cranium for use in the auxiliary points in the intermediate calculations involving the identification of the position of the detachable roentgenocontrast markers relative to the intracerebral reference points permits the roentgenography of the patient's head with the roentgenocontrast medium being injected into the cavities of his brain without having the detachable roentgenocontrast markers secured to his cranium. The absence of the detachable roentgenocontrast markers in the course of the contrast roentgenography allows one to choose any placement of the patient's head, including those which produce the best X-ray views of the intracerebral reference points.

It is desirable that the fastening of the detachable roentgenocontrast markers to the patient's cranium be effected by having the patient bite a dental impression of his upper jaw having these roentgenocontrast markers attached thereto.

This fastening is atraumatic and permits one to definitely secure the detachable roentgenocontrast markers to the patient's skull in the course of the roentgenographies as well as in the course of the stereotaxic operation for the purpose of orienting the intracerebric space physical model relative to the stereotaxic apparatus model.

The foregoing and other objects and advantages of the present invention will become more apparent from the ensuing detailed description of the embodiments thereof given by way example with reference being made to the accompanying drawings.

DETAILED DESCRIPTION OF THE EMBODIMENTS OF THE INVENTION

The procedure of guiding a stereotaxic instrument at an intracerebral space target point according to the invention is accomplished as follows.

A few days before, for example, a week before the forthcoming neurosurgical operation a roentgenocontrast medium, e.g. air, is injected through a lumbar puncture into the ventricles 1 (FIG. 1) of the patient's brain. It is permissible instead of air to inject into the cerebral cavities some other roentgenocontrast media—both gasiform and liquid, by means of a ventricular puncture.

Figure 1:
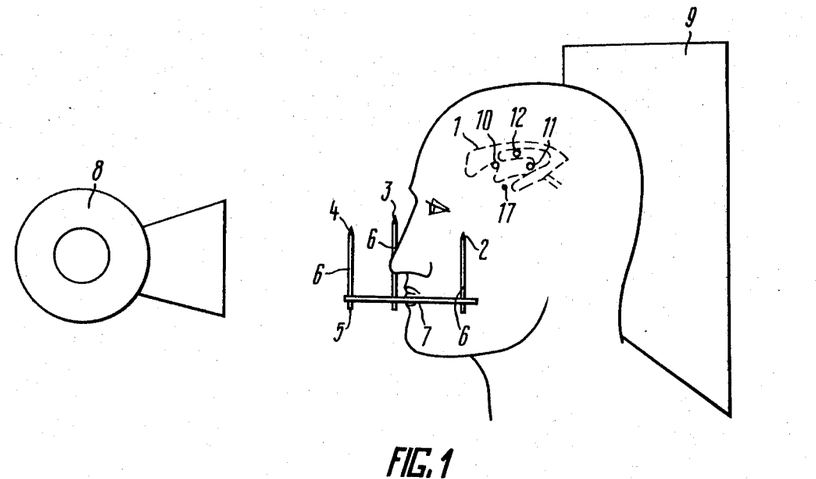
FIG. 1 represents the patient's head with the detachable roentgenocontrast markers secured to his cranium according to the invention.

Then four detachable roentgenocontrast point markers 2, 3, 4 and 5 are secured to the patient's head so that they assume a rigidly fixed position with regard to the patient's cranium. It is essential that the roentgenocontrast point markers 2, 3, 4 and 5 have such a relative position in which three of them, for instance, the markers 2, 3 and 4 are not arranged along one straight line. The detachable roentgenocontrast markers 2, 3, 4 and 5 are, for example, the points of metallic pins 6 attached to a plate 7 so that the distance between each of the two of the roentgenocontrast markers 2, 3, 4 and 5 can be measured easily and accurately. The plate 7 with the pins 6 is attached, for example, to a plaster dental impression of the patient's upper jaw, which allows the roentgenocontrast markers 2, 3, 4 and 5 to be rigidly secured to the patient's cranium inasmuch as the upper jaw remains stationary with regard to the cranium.

The plaster dental impression of the patient's upper jaw is made well in advance of the procedure described. For this purpose the patient bites a tray profiled according to the arch configuration of his upper jaw and filled with plaster. Thereafter the tray containing an impression is removed from the teeth and dried. When biting this impression the patient's upper jaw teeth fit individually in the corresponding indentations on the impression, owing to which the roentgenocontrast point markers 2, 3, 4 and 5 attached thereto assume one and the same reproducible spatial position relative to the patient's cranium at each biting of the impression. Such a manner of securing the detachable roentgenocontrast markers 2, 3, 4 and 5 is atraumatic and does not cause disagreeable sensations in the patient.

The securing of the detachable roentgenocontrast markers to the patient's cranium can be effected otherwise, for example, by means of placing in the bones of the patient's cranium two slots made of stainless steel, which are adapted to receive the pins carrying the plate with the roentgenocontrast markers. The slots are removed from the cranium after the operation.

In the embodiment of the invention described herein the number of the detachable roentgenocontrast markers 2-5 is equal to four. It should be borne in mind that the stated number is required as a minimum to practice the proposed method. According to the invention there may be provided more than four, e.g. five or six detachable roentgenocontrast markers and in this case the "redundant" roentgenocontrast markers, above the required four, can be used to check the results of the calculations involving the construction of the intracerebral space physical model as described below.

Then two roentgenographies of the patient's head are performed sequentially with the aid of a conventional diagnostic X-ray apparatus comprising one tube with the patient's head being placed arbitrarily and a known position of the roentgen radiation source 8 relative to a roentgen film 9. These two roentgenographies differ in projection conditions, that is in a relative position of the roentgen radiation source 8, the roentgen film 9 and the patient's head, with the placement of the patient's head being selected so as to provide in the roentgenograms images of the intracerebral reference points 10, 11 and 12, for example, anterior commissure, posterior commissure and vault apex respectively, and images of the detachable roentgenocontrast markers 2, 3, 4 and 5 carried by the plate 6. After the roentgenographies have been performed, the plaster impression with the roentgenocontrast markers 2, 3, 4 and 5 are taken off the patient's upper jaw.

In case it proves difficult to obtain in one roentgenogram the images of all the intracerebral reference points 10, 11 and 12, then the first and/or the second roentgenographies as are repeated many times as necessary in order to obtain in the total count at least two roentgenograms bearing an image of each intracerebral reference point, with all of the detachable roentgenocontrast markers 2, 3, 4 and 5 having to be shown in all of the roentgenograms.

Identification of the images of the detachable roentgenocontrast markers 2, 3, 4 and 5 in the roentgenograms is effected by their position relative to the image of the patient's cranium. It is also possible to identify the very images of the detachable roentgenocontrast markers 2-5 by providing the pins 6 with auxiliary elements, such as metallic rings, helical springs, etc., acting as identification marks.

Once the roentgenograms have been furnished, the calculations required to construct an intracerebral space physical model are carried out. These calculations amount to the following.

In each of the roentgenograms measurements are made of the coordinates of the central projections of the detachable roentgenocontrast markers 2, 3, 4 and 5, the central projections of the intracerebral reference points 10, 11 and 12, and the orthogonal projection of the roentgen radiation source 8 in an arbitrary coordinate system of the respective roentgenogram. The coordinate system of the roentgenogram is understood as a spatial rectangular coordinate system with one of its coordinate planes, for instance, the plane XOZ, coinciding with a plane of the roentgenogram.

By using the coordinates of the central projections of the detachable roentgenocontrast markers 2, 3, 4 and 5, of the central projections of the intracerebral reference points 10, 11 and 12 and of the orthogonal projection of the roentgen radiation source 8 in the roentgenogram available from the first roentgenography, as well as the known distance from the roentgen radiation source 8 to the roentgen film 9 in the course of the first roentgenography, in the coordinate system of the first roentgenography determined are the positions of imaginary straight lines extending across the roentgen radiation source 8 and each of the detachable roentgenocontrast markers 2-5, and the positions of imaginary straight lines extending across the roentgen radiation source 8 and each of the intracerebral reference points 10-12, with a relative position of the roentgen radiation source 8, the roentgen film 9 and the patient's head being such as it was in the course of the first roentgenography. Knowing the distances between each of the two of the detachable roentgenocontrast markers 2-5, the coordinates of these markers are determined in the coordinate system of the first roentgenogram, corresponding to their positions in the course of the first roentgenography.

Then a new coordinate system is introduced involving the detachable roentgenocontrast markers 2-5, for example, as follows: the axis OX extends across the markers 2 and 3 and is directed from the mark 3 to the mark 2, the beginning of the coordinate system corresponds to the middle of the segment joining said markers, the axis OY lies in the plane, wherein are arranged the markers 2, 3 and 4 not disposed along one straight line, and is directed to the marker 4, and the axis OZ is perpendicular to this plane and directed in accordance with the orientation chosen for the given coordinate system—right or left. In this coordinate system involving the roentgenocontrast markers 2-5 the positions of imaginary straight lines extending in the course of the first roentgenography across the roentgen radiation source 8 and across each of the intracerebral reference points 10-12 are determined with the aid of the known standard transformations associated with the conversion of data from one coordinate system to the other.

In the coordinate system of the roentgenogram available from the second roentgenography, by using the coordinates of the central projections of the detachable roentgenocontrast markers 2, 3, 4 and 5, of the central projections of the intracerebral reference points 10, 11 and 12 and of the orthogonal projection of the radiation source 8 in this roentgenogram, and by the known distance from the roentgen radiation source 8 to the roentgen film 9 in the course of the second roentgenography, determined are the positions of imaginary straight lines extending across the roentgen radiation source 8 and each of the detachable roentgenocontrast markers 2-5, and the positions of imaginary straight lines extending across the roentgen radiation source 8 and each of the intracerebral reference points 10-12, with a relative position of the roentgen radiation source 8, the roentgen film 9 and the patient's head being such as it was in the course of the second roentgenography. Knowing the distances between each of the two of the roentgenocontrast markers 2-5 and also the position of the mark 5 respective to the plane, wherein are arranged the markers 2,3 and 4 not disposed along one straight line, the positions of the markers 2, 3, 4 and 5 in the course of the second roentgenography are determined in the coordinate system of the second roentgenogram. Then in the coordinate system involving the roentgenocontrast markers 2-5 in a manner specified hereinabove are found the positions of the imaginary straight lines extending across the roentgen radiation source 8 and each of the intracerebral reference points 10-12 in the course of the second roentgenography.

Thus, in the coordinate system involving the detachable roentgenocontrast markers 2, 3, 4 and 5, the positions of the straight lines extending across the roentgen radiation source 8 and the intracerebral reference points 10, 11 and 12 in the course of the first and second roentgenographies have been obtained. It is apparent that the positions of the intracerebral reference points 10, 11 and 12 in this coordinate system will correspond to the point of intersection of each of the two of the imaginary straight lines connecting the roentgen radiation source 8 to one and the same intracerebral reference point. In this fashion the determination of the spatial position of the detachable roentgenocontrast markers 2, 3, 4 and 5 relative to the intracerebral reference points 10, 11 and 12 is accomplished. In addition to it, determined are the distances between the intracerebral reference points 10, 11 and 12, since the values of these distances in a given patient may differ from the values indicated in the stereotaxic atlas.

Then a coordinate system involving the intracerebral reference points 10, 11 and 12 is introduced, wherein are calculated the coordinates of the detachable roentgenocontrast markers 2, 3, 4 and 5, knowing the position of these markers relative to the intracerebral reference points 10, 11 and 12. The coordinate system involving the intracerebral reference points is constructed as follows: the axes OX and OZ lie in the mid-sagittal plane of the brain, with the axis OX extending across the anterior and posterior commissures and being directed to the anterior commissure, the axis OZ being directed to the patient's sinciput i.e. the forepart of the head, the beginning of the coordinate system corresponding to the middle of the segment joining the anterior and posterior commissures, while the axis OY being perpendicular to the mid-sagittal plane of the brain and directed from the left ear of the patient to his right ear. This coordinate system is equivalent to the coordinate system of the stereotaxic atlas.

However, as practice has shown, sometimes it proves difficult to perform the roentgenography of the patient's head with the roentgenocontrast markers 2-5 secured and the roentgenocontrast medium injected into the cavities of his brain. This may arise due to aggravation of the patient's condition after the injection of the roentgenocontrast medium, and the patient is liable to vomit or to lose consciousness, and he is rendered incapable of biting the plaster impression with the roentgenocontrast markers 2-5 attached thereto, and/or because the presence of the roentgenocontrast markers 2-5 secured to the patient's head does not permit him to place his head in a desired manner. If this is the case, the determination of the relative position of the detachable roentgenocontrast markers 2, 3, 4 and 5 and the intracerebral reference points 10, 11 and 12 is conducted as follows.

Prior to, for example, a month before the neutrosurgical operation, four complementary roentgenocontrast markers 13 (FIG. 2), 14, 15 and 16 are secured to the patient's cranium. These complementary roentgenocontrast markers are designed, as for example, miniaturized headed pins made of stainless steel. The heads of the pins are shaped so as to be readily discernible, for instance, triangular, round, horseshoe or rectangular. Spaced apart arbitrarily, the complementary roentgenocontrast markers 13, 14, 15 and 16 are secured in the external plate of the bones of the patient's cranium through miniature cutaneous cuts made under local anasthesia in the regions of the right and left sinciput protuberances and in the region of the forehead within the hair-covered portion of the head. The operation wounds are stitched up tightly. The complementary roentgenocontrast markers 13, 14, 15 and 16 do not cause discomfort in the patient leave no visible cosmetic deficiencies and hence are not removed subsequently.

It should be noted that in order to practice the proposed method, four complementary markers are to be provided as a minimum. In the patient's cranium there may be secured more than four complementary roentgenocontrast markers so as to use the "redundant" ones for checking the results of the calculations required to construct the intracerebral space physical model.

Figure 2:
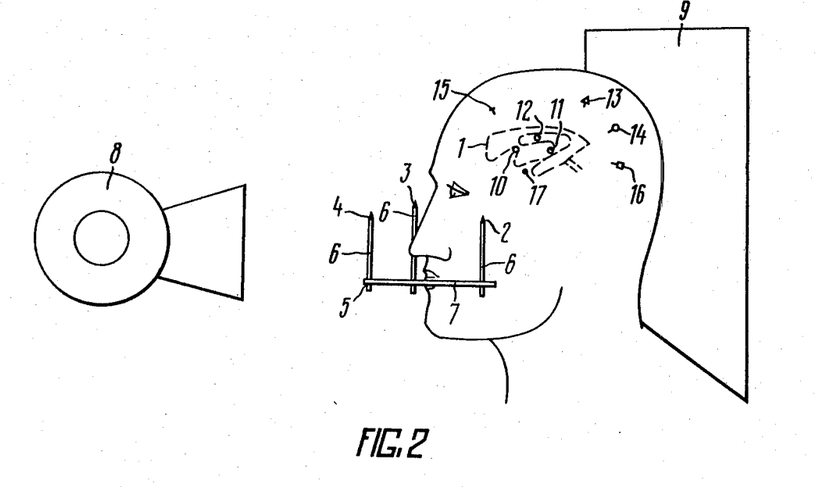
FIG. 2 represents the patient's head with the detachable roentgenocontrast markers secured to his cranium and the complementary roentgenocontrast markers fastened in the bones thereof according to the invention.

Then the detachable roentgenocontrast markers 2, 3, 4 and 5 are secured to the patient's cranium as described above, and two roentgenographies of the patient's head are performed sequentially in different projection conditions, with the patient's head being placed arbitrarily and with the known position of the roentgen radiation source 8 relative to the roentgen films 9. Subsequent to these roentgenographies, the detachable roentgenocontrast markers 2, 3, 4 and 5 are removed from the patient's head. The roentgenograms obtained provide the images of the detachable roentgenocontrast markers 2, 3, 4 and 5 and the complementary roentgenocontrast markers 13, 14, 15 and 16.

Further, a roentgenocontrast medium is injected into the ventricles 1 of the patient's brain and two more roentgenographies of the patient's head are performed sequentially in different projection conditions, with the patient's head being placed arbitrarily and with the known position of the roentgen radiation source 8 relative to the roentgen films 9. The roentgenograms obtained provide images of the complementary roentgenocontrast markers 13, 14, 15 and 16 and the intracerebral reference points 10, 11 and 12.

Indentification of the images of the roentgenoncontrast markers 13, 14, 15 and 16 secured within the cranium is ensured by virtue of the fact that each of these markers has a shape which is characteristic of and inherent in this or that marker only. Moreover, if the projection conditions in the course of the roentgenography are such that the shape of some of the complementary roentgenocontrast markers 13-16 become distorted at their projections in the roentgenograms and identification of these markers by the shape proves difficult, then the recognition of the complementary roentgenocontrast markers 13-16 is achieved in the course of the mathematical calculations described below while determining the relative spatial position of the detachable roentgenocontrast markers 2, 3, 4 and 5 and the complementary roentgenocontrast markers 13, 14, 15 and 16 secured within the cranium.

Similar to the case comsidered above, wherein the complementary roentgenocontrast markers 13, 14, 15 and 16 were not secured within the patient's cranium, it is essential that the following conditions be satisfied to provide the required amount of data for further calculations:

(1) as a result of the first two roentgenographies there should be produced in the total at least two roentgenograms with an image of each of the complementary roentgenocontrast markers 13-16, with all of the roentgenograms having to carry the images of all of the detachable roentgenocontrast markers 2-5; and (2) as a result of the second two roentgenographies there should be produced in the total at least two roentgenograms with an image of each of the intracerebral reference points 10-12, with all of the roentgenograms having to carry the images of all of the complementary roentgenocontrast markers 13-16.

It is to be understood that the sequence of performing said four roentgenographies is dependent on the specific conditions and it can be altered, that is it is permissible to start with roentgenographies of the patient's head with a roentgenocontrast medium injected into the cavities of his brain, and then to proceed to another two roentgenographies of the patient's head with the roentgenocontrast markers 2, 3, 4 and 5 secured on his upper jaw. To increase the effectiveness of the proposed method, it is important that the roentgenographies of the patient's head with a roentgenocontrast medium be carried out well in advance before the forthcoming neurosurgical operation requiring the procedure of guiding a stereotaxic instrument at a target point within the brain, so that by the start of the operation proper the changes of the spatial position of the cerebral structures caused by the injection of a roentgenocontrast substance into the cavities of the brain have disappeared completely.

In each of the roentgenograms available from the first two roentgenographies, measurements are made of the coordinates of the central projections of the complementary roentgenocontrast markers 13, 14, 15 and 16 secured in the cranium, the central projections of the detachable roentgenocontrast markers 2, 3, 4 and 5 and the orthogonal projection of the roentgen radiation source 8 in an arbitrary coordinate system of the respective roentgenogram.

In each of the roentgenograms available from the second two roentgenographies, measurements are made of the central projections of the complementary roentgenocontrast markers 13, 14, 15 and 16 secured in the cranium, the central projections of the intracerebral reference points 10, 11 and 12 and the orthogonal projection of the roentgen radiation source 8 in a coordinate system of the respective roentgenogram.

The processing of the data present in the roentgenograms available from these four roentgenographies is accomplished in a manner similar to that described hereinabove for the case in which only two roentgenographies of the patient's head were performed with the detachable roentgenocontrast markers 2, 3, 4 and 5 secured and a roentgenocontrast medium injected. More specifically, on the basis of the data present in the roentgenograms of the first two roentgenographies, the known distances between each of the two of the roentgenocontrast markers 2-5 and the known distance from the roentgen radiation source 8 to the roentgen films 9 in the course of the first two roentgenographies, in accordance with the technique described hereinabove, determined is the relative position of the detachable roentgenocontrast markers 2, 3, 4 and 5 and the complementary roentgenocontrast markers 13, 14, 15 and 16 secured in the cranium, and namely—the coordinates of the complementary roentgenocontrast markers 13, 14, 15 and 16 in the coordinate system involving, for instance, the detachable roentgenocontrast markers 2, 3, 4 and 5 as stated above. Along with that also determined are the distances between each of the two of the complementary markers 13, 14, 15 and 16.

On the basis of the data present in the roentgenograms of the second two roentgenographies, the calculated distances between the complementary roentgenocontrast markers 13, 14, 15 and 16 and the known distance from the roentgen radiation source 8 to the roentgen films 9 in the course of the second two roentgenographies, in accordance with the technique described hereinabove, determined is the relative position of the detachable roentgenocontrast markers 13, 14, 15 and 16 and the intracerebral reference points 10, 11 and 12, and namely—the coordinates of the intracerebral reference points 10, 11 and 12 in the coordinate system involving the detachable roentgenocontrast markers 13-16, for example, as follows: the axis OX extends across the markers 13 and 14, and is directed from the marker 14 to the marker 13, the beginning of the coordinate system corresponds to the middle of the section joining the markers 13 and 14, the axis OY lies in the plane, wherein arranged are the markers 13, 14 and 15, and is directed to the marker 15, while the axis OZ is perpendicular to this plane and directed according to the orientation chosen for the given coordinate system. Also determined are the distances between each of the two of the intracerebral reference points 10-12.

Subsequent to the determination of the relative position of the complementary roentgenocontrast markers 13-16 secured in the cranium and the detachable roentgenocontrast markers 2–5 (the coordinates of the markers 13–16 in the coordinate system involving the markers 2–5) and the relative position of the complementary roentgenocontrast markers 13–14 secured in the cranium and the intracerebral reference points 10–12 (the coordinates of the intracerebral reference points 10–12 in the coordinate system involving the markers 13–16) found is the relative position of the detachable roentgenocontrast markers 2, 3, 4 and 5 and the intracerebral reference points 10, 11, 12, and namely—the coordinates of the detachable roentgencontrast markers 2, 3, 4 and 5 in the coordinate system involving the intracerebral reference points 10, 11 and 12.

It is obvious that all of the abovestated calculating procedures resulting in the finding of the relative position of the detachable roentgenocontrast markers 2, 3, 4 and 5 and the intracerebral reference points 10, 11, and 12 can be described by the suitable equations solvable through the agency of an electronic computer in accordance with the program made up in advance. Hence, such calculations do not engage the surgeon's attention during the stereotaxic operation and can be performed beforehand with great accuracy outside the medical institution.

Then the coordinates of the target point 17 at which a stereotaxic instrument is to be guided in the neurosurgical operation are found out in the coordinate system defined by the intracerebral reference points 10, 11, 12. This is effected by means of locating the cerebral structure to be subjected to stereotaxic exposure in the stereotaxic atlas, selecting a target point within the scope of this structure and measuring the coordinates of this point in the coordinate system of the stereotaxic atlas. Further, the distance between the anterior and posterior commissures in the stereotaxic atlas is compared with the same distance determined in the calculations, a correction factor equal to the ratio of said distances is found and the coordinate X of the target point 17 determined according to the stereotaxic atlas is multiplied by this correction factor to produce the coordinates X of the target point 17 in the coordinate system involving the intracerebral reference points 10, 11 and 12. Similarly, a correction factor is found for the coordinate Z of the target point 17 determined according to the stereotaxic atlas, and the coordinate Z of the target point 17 is calculated in the coordinate system involving the intracerebral reference points 10, 11 and 12.

Figure 3:
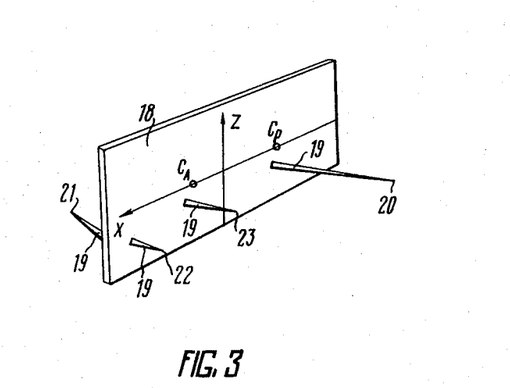
FIG. 3 represents the intracerebral space physical model according to the invention.

On the basis of the available data an intracerebral space physical model representing on a natural scale the relative position of the intracerebral reference points 10, 11 and 12, the target point 17 and the detachable roentgenocontrast markers 2, 3, and 4 secured to the cranium of the given patient is constructed. The intracerebral space physical model comprises a metallic plate 18 (FIG. 3) with its plane adapted to simulate the mid-sagittal plane of the patient's brain. The two coordinate axes OX and OZ of the coordinate system defined by the intracerebral reference points 10 (FIGS. 1, 2), 11 and 12 are plotted on the metallic plate 18. Pointed metallic pins 19 are attached perpendicularly to the surface of said plate 18 (FIG. 3). Points 20, 21 and 22, positioned on the pointed edges of the metallic pins 19, are adapted to simulate the roentgenocontrast markers 2 (FIGS. 1, 2), 3 and 4 respectively, while a point 23 (FIG. 3) is adapted to simulate the target point 17 (FIGS. 1, 2), i.e. the points 20 (FIG. 3), 21, 22 and 23 have the coordinates in the coordinate system involving the intracerebral reference points 10 (FIGS. 1, 2), 11, 12 identical to those of the roentgenocontrast markers 2, 3, 4 and the target point 17 respectively.

Figure 4A:
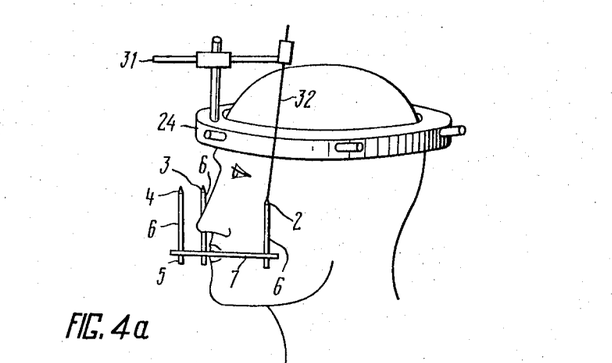
FIGS. 4a, b, c represent the patient's head with the stereotaxic apparatus placed thereon and the deatachable roentgenocontrast markers secured to his cranium.
Figure 5A:
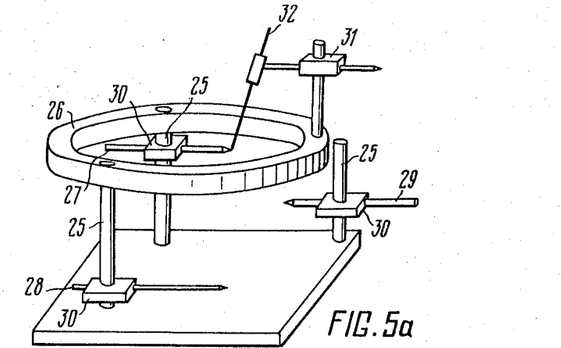
FIGS. 5a, b, c diagrammatically represent the fixing of the specified positions of the detachable roentgenocontrast markers relative to the stereotaxic apparatus in the stereotaxic apparatus model according to the invention.

A base ring 24 (FIG. 4a) of the stereotaxic apparatus is fastened on the patient's head before the start of the neurosurgical operation. On supports 25 (FIG. 5a), disposed separately from the patient, is mounted a stereotaxic apparatus model comprising a ring 26 being an exact counterpart of the base ring 24 (FIG. 4a) of the stereotaxic apparatus, and three bars 27 (FIG. 5a), 28 and 29 mounted in bushings 30 so as to be movable along and rotatable on the supports 25.

The patient bites his plaster impression of the upper jaw teeth with the roentgenocontrast markers 2 (FIG. 4a), 3, 4 and 5 secured thereto, with the markers 2, 3, 4 and 5 assuming the same position relative to the patient's cranium as they had in the course of the first two roentgenographies. Then determined are the positions of the detachable roentgenocontrast markers 2, 3 and 4, which are simulated in the intracerebral space physical model, relative to the stereotaxic apparatus. With this purpose in view, on the base ring 24 of the stereotaxic apparatus is mounted a guiding arrangement 31 with a stereotaxic instrument 32 and the end of the instrument 32 is adjusted, for example, to the roentgenocontrast marker 2, with the position of the stereotaxic instrument 32 being fixed at the guiding arrangement 31, whereupon the guiding arrangement 31 with the stereotaxic instrument 32 in the fixed position is transferred from the base ring 24 of the stereotaxic apparatus onto the ring 26 (FIG. 5a) of the stereotaxic apparatus model and is mounted in a manner similar to that when it was located on the base ring 24 (FIG. 4a) of the stereotaxic apparatus. One of the bars of the stereotaxic apparatus model, for instance, the bar 27 (FIG. 5a) is moved along the support 25 and rotated thereabout thereof so that the pointed edge of the bar 27 is adjusted to the end of the stereotaxic instrument 32, whereafter the resultant position of the bar 27 is fixed at the support 25.

Figure 4B:
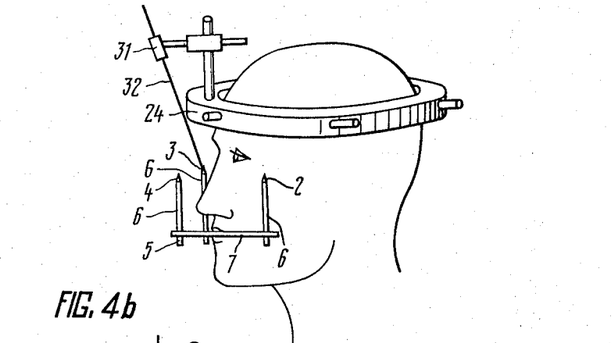
Figure 4C:
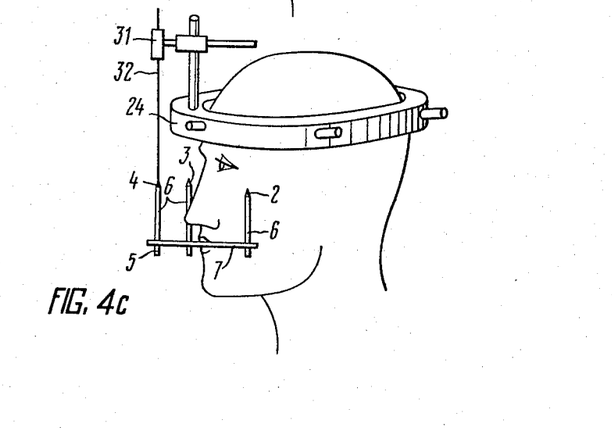
Figure 5B:
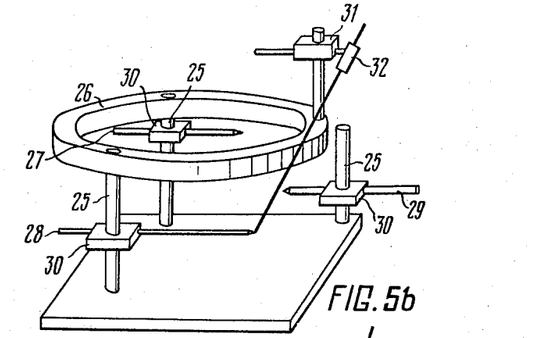
Figure 5C:
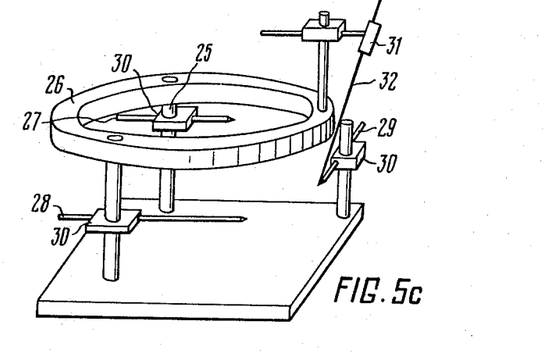

Then the guiding arrangement 31 with the stereotaxic instrument 32 is again transferred onto the base ring 24 (FIG. 4b) of the stereotaxic apparatus and the end of the instrument 32 is adjusted, for example, to the roentgenocontrast marker 3, with the position of the stereotaxic instrument 32 being fixed at the guiding arrangement 31. The guiding arrangement 31 is transferred from the base ring 24 of the stereotaxic apparatus onto the ring 26 (FIG. 5b) of the stereotaxic apparatus model and the end of the stereotaxic instrument 32 is adjusted to the pointed edge, for instance, of the bar 28, while fixing the position thereof at the support 25. And lastly, the guiding arrangement 31 with the stereotaxic instrument 32 is again mounted on the base ring 24 (FIG. 4c) of the stereotaxic apparatus, the end of the stereotaxic instrument 32 is adjusted to the roentgenocontrast marker 4 and the position of the instrument 32 is fixed. Then, the guiding arrangement 31 with the stereotaxic instrument 32 is transferred onto the ring 26 (FIG. 5c) of the stereotaxic apparatus model and the end of the instrument 32 is adjusted to the pointed edge of the bar 29, while fixing the position thereof at the support 25.

Thus, the sequential adjustments of the stereotaxic instrument 32 (FIG. 4) to the roentgenocontrast markers 2, 3 and 4 and the transference of the instrument 32 fixed in the specified positions onto the ring 26 (FIG. 5) of the stereotaxic apparatus model result in that the pointed edges of the bars 27, 28 and 29 assume the same spatial position relative to the stereotaxic apparatus model as the roentgenocontrast markers 2 (FIG. 4), 3 and 4 correspondingly assume relative to the stereotaxic apparatus, that is the fixing of the positions of the roentgenocontrast markers 2, 3 and 4 relative to the stereotaxic apparatus in the stereotaxic apparatus model is thereby achieved.

Apparently, at each transference of the guiding arrangement 31 with the stereotaxic instrument 32 from the base ring 24 of the stereotaxic apparatus onto the ring 26 (FIG. 5) of the stereotaxic apparatus model, the mounting site of the guiding arrangement 31 on the ring 26 should correspond to the mounting site of the guiding arrangement 31 on the base ring 24 (FIG. 4) of the stereotaxic apparatus.

The fixing of the positions of the roentgenocontrast markers 2 (FIG. 4), 3 and 4 in the stereotaxic apparatus model can be effected in a different manner. For instance, use could be made of two identical guiding arrangements with an instrument, one of which is mounted on the stereotaxic apparatus and the other is mounted on the stereotaxic apparatus model. Both of the guiding arrangements are provided with scales for measuring the movements of the stereotaxic instrument and the elements of the guiding arrangement relative to the stereotaxic apparatus and its model. In this case, when the instrument is adjusted to any of the roentgenocontrast markers, readings are taken from the scales of the guiding arrangement of the stereotaxic apparatus and the guiding arrangement and the stereotaxic instrument are set forth on the stereotaxic apparatus model in accordance with these readings, with the same scales of the stereotaxic apparatus model being employed.

The guiding arrangements on the stereotaxic apparatus and on the model thereof can also be associated with each other mechanically, for example, by means of a pantograph, or electrically, for example, by means of movement pick-ups and selsyns, so that any alteration of the position of the stereotaxic instrument on the apparatus would result in the same alteration of the position of the stereotaxic instrument on the apparatus model.

Figure 6:
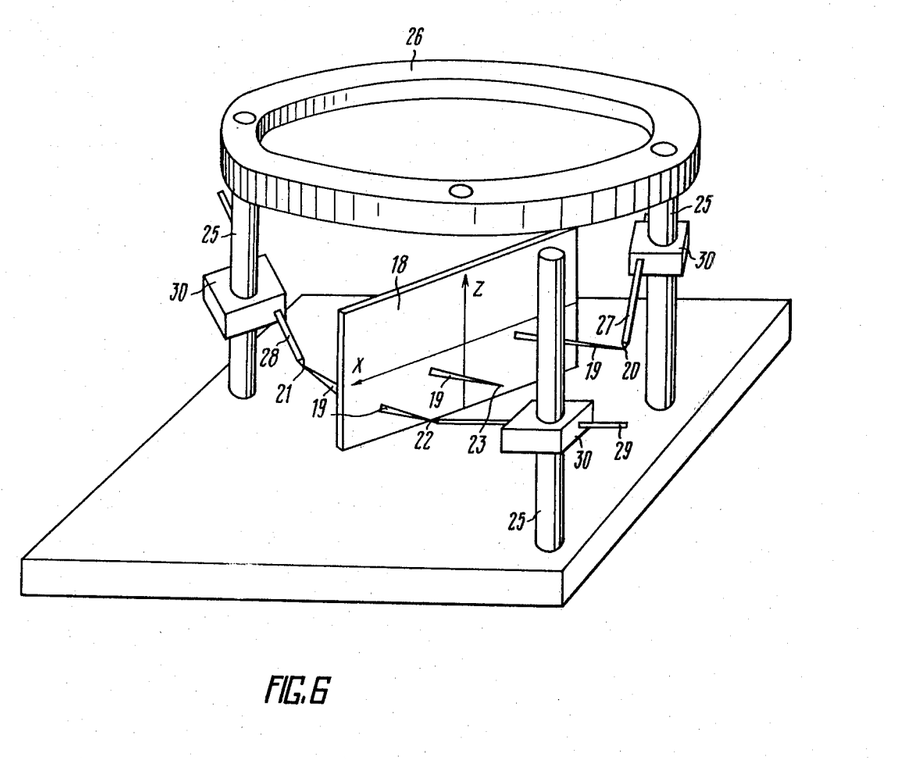
FIG. 6 is a perspective view of the intracerebral space physical model oriented relative to the stereotaxic apparatus model according to the invention.

Then the plate 18 (FIG. 6) is set in the stereotaxic apparatus model so as to adjust the points 20, 21 and 22 to the pointed edges of the bars 27, 28 and 29 respectively, and the plate 18 is fixed in this position. As a result, the spatial position of the plane of the plate 18 and the points 20, 21 and 22 relative to the ring 26 will be identical to the spatial position of the mid-sagittal plane of the patient's brain and the roentgenocontrast markers 2 (FIG. 4), 3 and 4 relative to the base ring 24 of the apparatus, i.e. the orientation of the intracerebral space physical model relative to the stereotaxic apparatus model is thereby achieved.

Figure 7:
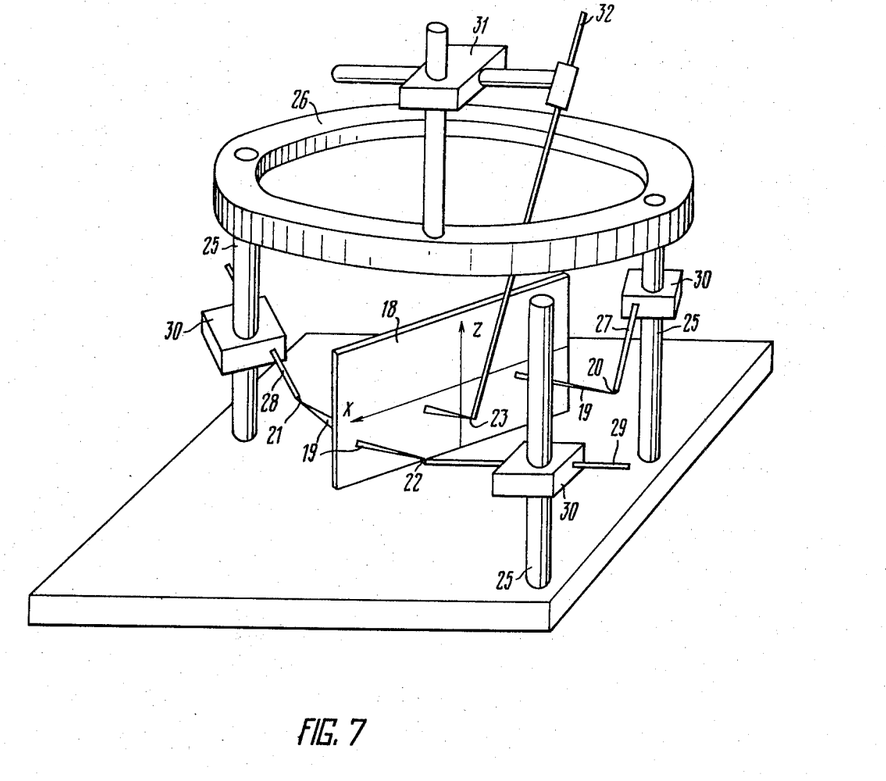
FIG. 7 diagrammatically represents the means for adjusting the stereotaxic instrument to the point of the intracerebral space physical model adapted to simulate the target point according to the invention.

Further, the guiding arrangement 31 (FIG. 7) with the stereotaxic instrument 32 are mounted on the ring 26 of the stereotaxic apparatus model and the operative end of the stereotaxic instrument 32 is adjusted to the point 23 of the intracerebral space physical model adapted to simulate the target point 17 (FIGS. 1, 2) of the patient's intracerebral space. The position of the instrument 32 (FIG. 7) resulting from the adjustment is fixed at the guiding arrangement 31 and the guiding arrangement 31 with the stereotaxic instrument 32 in the fixed position is transferred onto the base ring 24 (FIG. 8) of the stereotaxic apparatus.

Figure 8:
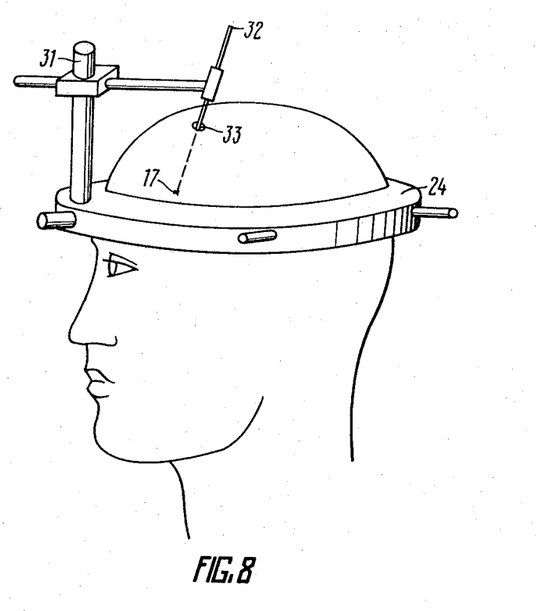
FIG. 8 shows the patient's head with a trepanation aperture and the stereotaxic instrument introduced thereinto.

Then a trepanation aperture 33 is made and the stereotaxic instrument is introduced thereinto, which results in the operative end of the stereotaxic instrument 32 being adjusted to the target point 17 of the patient's intracerebral space.

The proposed method of guiding the stereotaxic instrument at an intracerebral space target point in comparison with the prior art methods offers the following advantages:

(a) provision for repeatedly securing the detachable roentgenocontrast markers to the patient's cranium required for the orientation of the intracerebral space physical model relative to the stereotaxic apparatus model, and sequentially adjusting the stereotaxic instrument to the point of the intracerebral space physical model, adapted to simulate the target point, and to the target point of the intracerebral space in an arbitrarily large time interval after the accomplishment of the foregoing procedures of injecting a roentgenocontrast medium into the cavities of the patient's brain, performing roentgenographies of the patient's head and simulating the intracerebral space. This allows one:

to increase the accuracy of guiding the stereotaxic instrument at the target point in question. When tested on corpses, the proposed method enabled one to accurately reach the target point 56 times out of the total 58 times of guiding the stereotaxic instrument;

to reduce the traumatic level of the guiding procedure inasmuch as there is no need for making a separate trepanation aperture for the injection of a roentgenocontrast medium, no need for rigidly fastening the patient's head to the operation table in the course of the roentgenographies performed, and also owing to the absence of the roentgen exposure of the patient at the time of adjusting the stereotaxic instrument to the target point of the intracerebral space;

to reduce the time taken by the procedures involving the manipulations on the patient; the procedure of adjusting the stereotaxic instrument to one target point takes about twenty minutes;

to provide for sequentially guiding the stereotaxic instrument at a large number of target points due to the reduction of the time required for guiding;

to remove the need for a specialized operating room equipped with X-raying instrumentation since the necessary roentgenographies are performed well in advance of the stereotaxic operation;

to use the available X-raying instrumentation in the best way possible and with maximum loading since the X-raying instrumentation is not located in the operating room; and to utilize a conventional diagnostic X-raying apparatus comprising a single tube when performing the roentgenographies since there is no necessity for X-raying with two tubes at one time.

(b) Freedom from the need for accurately placing the patient's head respective to the X-raying apparatus and the film in the course of the roentgenographies, which enables one:

to further increase the accuracy of guiding the stereotaxic instrument since the prior art methods presuppose the necessity of accurately placing the patient's head, the ideal accomplishment of which is actually impracticable; and to entrust X-raying operators with the performance of the roentgenographies of the patient's head without any special extra training.

The proposed method has been tested at a clinic on three patients suffering from multifocal epilepsy. A group of stereotaxic instruments—long-term multiple electrodes—have been introduced into various cerebral structures of the patients for diagnostic and therapeutic purposes. Each of these three patients had a disease of long standing (not less than ten years) with frequent seizures and drug therapy was of no avail to these patients.

In the capacity of the target structures there were selected the symmetrical formations of the temporal lobes-amygdala, hippocampus, the uncus of the hippocampal gyrus, and also the structures of the thalamus and hypothalamus, several areas of the cortex, all in all 8-14 structures. The selection of the target structures was made with consideration of the data of a complex study, the structure of epileptic seizures and the nature of the electroencephalography. Teflon-insulated gold electrodes of a 0.1 mm diameter were used, with six electrodes combined into a bundle, wherein the active ends of the electrodes were arranged "stepwise" with a spacing of 3 mm.

Subsequent to the identification of the target structures, four complementary roentgenocontrast markers were introduced through miniature cuts of a 2-2.5 cm. length under local anaesthesia into the cortical layer of the bones of each patient's cranium in the regions of the right and left parietal protuberances, in the region of the forehead along the midline on the border of the hair-covered portion of the head, and also in the region of the occipital protuberances. The operation wounds were stitched up tightly. The first and second roentgenographies were performed in a sedentary position with the aid of a RUM-22A X-raying apparatus with a single tube. The roentgenocontrast medium, specifically air, was injected through a lumbar puncture in an amount of 40-60 cm$^3$. A lateral placement of the head and a three quarter placement with a focal distance of 1-1.2 m. were used. In the cases when such placing modes did not permit one to obtain adequate contrast views of the intracerebral reference points, specifically, the anterior and posterior commissures, additional placing modes were used, specifically front-back in a sedentary position and the same placing modes in a supine position.

After the consequences of the injection of the roentgenocontrast medium have completely vanished (3-10 days) in the patients, dental impressions of the upper jaw were made. With this purpose in view a tray, profiled according to the arch configuration of the upper jaw, was filled with a plaster solution. The patient bit the plaster-filled tray, whereafter the tray was taken off and dried.

The third and fourth roentgenographies were performed with the aid of a RUM-22A X-raying apparatus in a sedentary position in a lateral projection and a three quarter projection respectively. Immediately before the roentgenographies the patient bit the tray with the dental impression of his upper jaw with four detachable roentgenocontrast markers secured thereon.

The coordinates of the target points were determined by the 1959 stereotaxic atlas of Shaltenbrandt and Baily. The resultant data together with the coordinates of the intracerebral reference points, the detachable roentgenocontrast markers and the complementary roentgenocontrast markers, measured in the roentgenograms, were introduced to a Minsk-32 electronic computer.

The computation results, specifically the coordinates of the target points and the detachable roentgenocontrast markers in the coordinate system prescribed by the intracerebral reference points, were used for the purpose of constructing an intracerebral space physical model.

The neurosurgical operation was carried out 1-1.5 months after the procedure of securing the complementary roentgenocontrast markers in the bones of the patients' cranium. The operation was conducted in a conventional operating room without any X-raying facilites installed therein. The base ring of the stereotaxic apparatus was fastened on the patient's head under local anaesthesia, whereafter the patient bit the dental impression of his upper jaw with the detachable roentgenocontrast markers. A guiding arrangement with a stereotaxic instrument was mounted on the base ring, the end of the stereotaxic instrument was adjusted to one of the detachable roentgenocontrast markers. The position of the elements of the guiding arrangement was fixed, whereafter the guiding arrangement was separated from the stereotaxic apparatus and mounted on a stereotaxic apparatus model. The pointed edge of one of the movable bars, mounted on the stereotaxic apparatus was adjusted to the end of the stereotaxic instrument and the position of this bar was fixed, while the guiding arrangement was transferred onto the stereotaxic apparatus for adjusting the end of the stereotaxic instrument to another detachable roentgenocontrast marker. The abovedescribed procedures were repeated with application to the other two detachable roentgenocontrast markers. Subsequently, the intracerebral space physical model was located so that its points, adapted to simulate the detachable roentgenocontrast markers, were adjusted to the pointed edges of the respective movable bars of the stereotaxic apparatus model, and the intracerebral space physical model was fixed in this position relative to the stereotaxic apparatus model. This preparatory part of the operation took 15-20 minutes on the average.

Then the guiding arrangement with the stereotaxic instrument was mounted on the stereotaxic apparatus model, the operative end of the stereotaxic instrument was adjusted to one of the points of the intracerebral space physical model adapted to simulate one of the target points, the position of the elements of the guiding arrangement was fixed and the guiding arrangement was transferred onto the ring of the stereotaxic apparatus. Cuts in the soft tissue of the head were made under local anaesthesia, trepanation of the cranial bones and coagulation of the cerebral meninges were effected. The electrode bundle was then introduced into the target structure and fastened to the bone edges of the trepanation aperture with Noracryl rapid-setting plastic. The introduction of the electrodes into the other target points was accomplished similarly. The introduction of the electrode bundle into the target structure took, on average, 10-20 minutes.

After the completion of the operation, the wounds were stitched up. The extracranial ends of the introduced electrodes were brought out to the corners of the wounds. On the termination of a post-operational period, the patients were X-rayed to determine how accurately the electrodes had reached the target structures. Subsequently, the recording of the bioelectric phenomena from the introduced electrodes was made followed by diagnostic and curative stimulations and destruction of the revealed epileptic foci.

The accuracy of reaching the target structures by the electrodes was verified in each of the three operated patients by means of checking roentgenographies and physiological control. It was also verified by the decreased number or complete disappearance of the seizures after the operation, as well as the high effectiveness of the curative procedures through the electrodes.

The aforedescribed embodiments of the present invention have been presented hereinabove exclusively for illustrative purposes and are not to be interpreted as limiting the scope thereof. Various changes and other embodiments of the proposed method are possible without departing from the spirit and scope of the invention defined by the appended claims.

What is claimed is:

1. A method of guiding a stereotaxic instrument at an intracerebral space target point, comprising the steps of:

injecting a roentgenocontrast medium into the cerebral cavity of a patient to produce contrast of the intracerebral points thereof;

securing to the patient's cranium at least four detachable roentgenocontrast markers having known distances therebetween, with one of said detachable roentgenocontrast markers being offset from a straight line joining any two of other said detachable roentgenocontrast markers;

effecting a first roentgenography of the patient's head;

effecting a second roentgenography of the patient's head with said second roentgenography being effected under projection conditions differing from projection conditions of said first roentgenography;

removing said detachable roentgenocontrast markers from the patient's head;

identifying a position of said detachable roentgenocontrast markers relative to said intracerebral points as references by using the roentgenograms available from said first and second roentgenographies, the distances between said detachable roentgenocontrast markers and the positions of the roentgen radiation source relative to the roentgen films in the course of said first and second roentgenographies;

identifying a position of the intracerebral space target point relative to said intracerebral reference points;

constructing an intracerebral space physical model presenting the relative position of said intracerebral reference points, said detachable roentgenocontrast markers and said target point, said intracerebral space physical model including at least three points, each of which is adapted to simulate one of said detachable roentgenocontrast markers, and a point adapted to simulate said target point;

placing a sterotaxic apparatus on the patient's head;

recurrently securing to the patient's cranium said detachable roentgenocontrast markers in exactly the same position as they had relative to the patient's cranium in the course of said first and second roentgenographies;

identifying the positions of said detachable roentgenocontrast markers, simulated in said intracerebral space physical model, relative to said stereotaxic apparatus and fixing in a stereotaxic apparatus model these indicated positions of said detachable roentgenocontrast markers relative to said stereotaxic apparatus;

orienting said intracerebral space physical model relative to said stereotaxic apparatus model by placing said three points of said intracerebral space physical model adapted to simulate said detachable roentgenocontrast markers in the specified positions of said detachable roentgenocontrast markers relative to said stereotaxic apparatus set forth in said stereotaxic apparatus model;

mounting a guiding arrangement with a stereotaxic instrument upon said stereotaxic apparatus model and adjusting an operative end of said stereotaxic instrument to the specified point of said intracerebral space physical model adapted to simulate the specified target point, with the position of said stereotaxic apparatus being rigidly secured at said guiding arrangement;

drilling a trepanation aperture; and mounting said guiding arrangement with said stereotaxic instrument upon said stereotaxic apparatus and introducing said stereotaxic instrument into said trepanation aperture.

2. A method of guiding a stereotaxic instrument as recited in claim 1, wherein the step of identifying positions of said detachable roentgenocontrast markers, simulated in said intracerebral space physical model, relative to said stereotaxic apparatus and fixing in a stereotaxic apparatus model these specified positions of said detachable roentgenocontrast markers relative to said stereotaxic apparatus, is effected by sequential adjustments of the stereotaxic instrument to said detachable roentgenocontrast markers while securing the position of said stereotaxic instrument at the guiding arrangement at each such adjustment and transferring said guiding arrangement with said stereotaxic instrument following each such adjustment from said stereotaxic apparatus onto said stereotaxic apparatus model.

3. A method of guiding a sterotaxic instrument as recited in claim 2, wherein the steps of:

securing to the patient's cranium said detachable roentgenocontrast markers is preceded by fastening at least four complementary roentgenocontrast markers in the bones of his cranium, which is followed by performing said first and second roentgenographies;

injecting a roentgenocontrast medium into the cerebral cavity of the patient is effected subsequent to performing said first and second roentgenographies and removing said detachable roentgenocontrast markers from the patient's head;

injecting a roentgenocontrast medium into the cerebral cavity of the patient is followed by performing third and fourth roentgenographies of the patient's head, with said third roentgenography differing in projection conditions from said fourth roentgenography;

identifying a position of said detachable roentgenocontrast markers relative to said intracerebral reference points is effected on the basis of said four roentgenographies by identifying a position of said detachable roentgenocontrast markers relative to said complementary roentgenocontrast markers and identifying a position of said complementary roentgenocontrast markers relative to said intracerebral reference points, with distances between said complementary roentgenocontrast markers being calculated while identifying a position of said detachable roentgenocontrast markers relative to said complementary roentgenocontrast markers; a position of said detachable roentgenocontrast markers relative to said complementary roentgenocontrast markers being identified by using the roentgenograms available from said first and second roentgenographies, distances between said detachable roentgenocontrast markers and positions of the roentgen radiation source relative to the roentgen films in the course of said first and second roentgenographies; while a position of said complementary roentgenocontrast markers relative to said intracerebral reference points being identified by using the roentgenograms available from said third and fourth roentgenographies, distances between said complementary roentgenocontrast markers and positions of the roentgen radiation source relative to the roentgen films in the course of said third and fourth roentgenographies.

4. A method of guiding a stereotaxic instrument as recited in claim 3, wherein the step of securing said detachable roentgenocontrast markers to the patient's cranium is effected by the patient's biting a dental impression of his upper jaw having said detachable roentgenocontrast markers clamped thereto.

5. A method of guiding a stereotaxic instrument as recited in claim 1, wherein the steps of:

securing to the patient's cranium said detachable roentgenocontrast markers is preceded by fastening at least four complementary roentgenocontrast markers in the patient's skull which is followed by performing said first and second roentgenographies;

injecting a roentgenocontrast medium into the cerebral cavity of the patient is effected subsequent to performing said first and second roentgenographies and removing said detachable roentgenocontrast markers from the patient's head;

injecting a roentgenocontrast medium into the cerebral cavity of the patient is followed by performing third and fourth roentgenographies of the patient's head, said third roentgenography differing in projection conditions from said fourth roentgenography; identifying a position of said detachable roentgenocontrast markers relative to said intracerebral reference points is effected on the basis of said four roentgenographies by identifying a position of said detachable roentgenocontrast markers relative to said complementary roentgenocontrast markers and identifying a position of said complementary roentgenocontrast markers relative to said intracerebral reference points, with distances between said complementary roentgenocontrast markers being calculated while identifying a position of said detachable roentgenocontrast markers relative to said complementary roentgenocontrast markers; a position of said detachable roentgenocontrast markers relative to said complementary roentgenocontrast markers being identified by using the roentgenograms available from said first and second roentgenographies, distances between said detachable roentgenocontrast markers and positions of the roentgen radiation source relative to the roentgen films in the course of said first and second roentgenographies; while a position of said complementary roentgenocontrast markers relative to said intracerebral reference points being identified by using the roentgenograms from said third and fourth roentgenocontrast markers and positions of the roentgenradiation source respective to the roentgen films in the course of said third and fourth roentgenographies.

6. A method of guiding a stereotaxic instrument as recited in claim 1, wherein the step of securing said detachable roentgenocontrast markers to the patient's cranium is effected by the patient's biting a dental impression of his upper jaw having said detachable roentgenocontrast markers clamped thereto.

* * * * *